United States Patent [19]

Nicolas et al.

[11] 4,298,686
[45] Nov. 3, 1981

[54] METHOD OF IMMUNOENZYMATIC ASSAY UTILIZING $\Delta_5$,3-KETO-STEROID ISOMERASE

[75] Inventors: Jean C. Nicolas; Beatrice Terouanne; Bernard Descomps; Andre C. De Paulet, all of Montpellier, France

[73] Assignee: Institut National de la Sante et de la Recherche Medicale (INSERM), Paris, France

[21] Appl. No.: 60,677

[22] Filed: Jul. 25, 1979

[30] Foreign Application Priority Data

Aug. 2, 1978 [FR] France .................. 78 22867

[51] Int. Cl.³ .................. G01N 33/54; C12N 9/96
[52] U.S. Cl. .................. 435/7; 435/188; 435/233; 424/12; 23/230 B
[58] Field of Search .................. 435/7, 188, 174, 177, 435/805, 810, 233, 181; 23/230 B; 424/12

[56] References Cited

U.S. PATENT DOCUMENTS

| | | | |
|---|---|---|---|
| 3,879,262 | 4/1975 | Schuurs et al. | 435/181 |
| 3,948,728 | 4/1976 | Röeschlau et al. | 435/233 |
| 4,002,532 | 1/1977 | Weltman et al. | 435/188 |
| 4,048,416 | 9/1977 | Axen et al. | 435/181 |
| 4,062,733 | 12/1977 | Edwards et al. | 435/7 |
| 4,067,774 | 1/1978 | Rubenstein et al. | 435/7 |
| 4,069,106 | 1/1978 | Stanley et al. | 435/177 |
| 4,166,104 | 8/1979 | Wagner et al. | 23/230 B |
| 4,218,539 | 8/1980 | Weltman | 435/188 |

OTHER PUBLICATIONS

Jones, et al., "Steroids and Steroidases. IX." *Canadian J. Chem.*, vol. 47, (1969) pp. 4459–4466.

Benson, et al., "Role of Reduced Glutothione in $\Delta^s$-3-Ketosteroid Isomerase Reaction of Liver", *Biochem. Biophys. Res. Comm.*, vol. 69, No. 4 (1976) pp. 1073–1079.

Nicolas, et al. "New Amplification System for the Enzymic Determination of Microquantities of NAb (H): Applications and Perspectives", *Chem. Abstracts*, vol. 90, No. 1 p. 269 (1979) Abs. No. 2711q.

*Primary Examiner*—Thomas G. Wiseman
*Attorney, Agent, or Firm*—Oblon, Fisher, Spivak, McClelland & Maier

[57] ABSTRACT

The invention relates to a novel enzymatic labelling agent for immunoenzymatic assays. The labelling agent is $\Delta_5$, 3-keto-steroid isomerase. The enzymatic activity bound to the antibody can be revealed advantageously by: (1) direct reading on the supernatent liquor or on the cake obtained by precipitation by means of a solvent, such as polyethylene glycol, with the use of soluble antibodies; (2) reading in solution after liberation of the enzyme from the antigen-antibody complex by a reducing agent, such as dithiotreitol; (3) immediate reading after filtration of a substrate solution on the insolubilized antibody-antigen-enzyme complex. The method can be used for immunoenzymatic assays automatically on substances present in very low concentrations, such as hypophysial hormones and plasmatic steroids.

16 Claims, 6 Drawing Figures

FIG.1

METHOD OF IMMUNOENZYMATIC ASSAY UTILIZING $\Delta_5$,3-KETO-STEROID ISOMERASE

BACKGROUND OF THE INVENTION

1. Field of the Invention

The present invention relates to the field of immunoenzymatic assays, also named enzyme immuno-assays.

2. (EIA) Description of the Prior Art

Methods of radio-immunological assay/(RIA) have long been known for the quantitative determination of the concentration of certain substances in biological media, in particular of antigens or of antibodies as well as of certain hormones. However, methods of radio-immunological assay present drawbacks. Among the latter, must be stressed the restrictions in practice which are involved in the use of radioactive labelling agents, which do not permit the method to be accessible to any laboratory indiscriminately.

During the last ten years, important advances accomplished in enzymology have enabled the substitution for radio-immunological assays of immunoenzymatic assays which resort to an enzyme as a labelling agent instead of the radioactive labelling agents previously used. There are numerous bibilographic references in the field of immunoenzymatic assays; it suffices to refer, for example, to the article of S. AVRAMEAS "Detection of Antibodies and Antigens by Means of Enzymes", Bull. Soc. Chim. Biol., 1968, 50, No. 5-6 as well as to the French Patent Applications Nos. 74.34.519 and 75.36.889.

A certain number of immunoenzymatic assay methods exist.

For example, if the method is used for determining antibodies, a method of procedure comprises the steps of incubating the antibodies to be assayed with an insolubilized antigen, of washing the solid phase after removal of the supernatant liquors, of incubating the solid phase with an antibody labelled by means of an enzyme, and of measuring the enzymatic activity of the solid phase.

In such a method it is possible to utilize any insoluble support on which the antibody is fixed by known means.

In another method called, a "sandwich assay", applied for example, to the determination of antibodies, the following succession of steps is used:

incubating the antibodies to be tested with an antigen rendered insoluble, washing the solid phase after removal of the supernatant liquors, and incubating the solid phase with an antigen coupled with an enzyme.

It is also known that the measurements may be carried out by means of the same processes not in the solid phase but in the liquid phase. In all cases, it is the enzymatic activity of the selected phase which is the determinant parameter of the assay.

All the above indications are well-known to the one skilled in the art and have only been given to illustrate the field to which the present invention is applicable.

The method of immunoenzymatic assay has the advantage of being applicable without particular restrictions, which is not the case with radioimmunological assays. However, the practical application of immunoenzymatic assays again raises certain difficulties. In fact, the method is limited as to its sensitivity and does not permit detection of very small amounts of antigen, of antibodies or of hormones in the biological media to be tested. Hence, there exist also cases where, at the present time, no assay method is available if the concentration of the active substance to be measured is too low. It is also important to apply improvements to the methods of coupling between antigens and antibodies with the enzymes, respectively, to improve the fixation yields and to avoid interfering secondary reactions. Finally, problems of stability of the enzyme labelling agents in the course of time may also arise.

SUMMARY OF THE INVENTION

It is an object of the invention to provide a method of immunoenzymatic assay which, due to the use as a labelling agent of a particularly suitable enzyme, enables measurements to be carried out with sensitivities never attained hitherto, which offers the possibility of carrying out assays which could not be carried out up to the present time.

It is also an object of the invention to provide a method of immunoenzymatic assay which, due to the application of said enzyme, lends itself to complete automation in already existing equipment and that used for radioimmunological assays.

It is also an object of the invention to provide a method of immunoenzymatic assay which, due to the particular properties of the enzyme concerned, can be applied without it being necessary to pass through a prior step of insolubilizing the active substance to be determined, for example, of the antibody or of the antigen.

It is a further object of the invention to provide a particular method of coupling the antigen and the antibody with the enzyme concerned, said coupling being effected selectively and with high yield.

DETAILED DESCRIPTION OF THE INVENTION

In its most general form, the invention provides a method of immunoenzymatic assay comprising utilizing $\Delta_5$,3-keto-steroid isomerase as an enzymatic labelling agent the enzymatic activity, which constitutes a value representative of the concentration of the substance to be measured, being determined by measurement of the absorption in the ultraviolet at 248 nm.

It is not a prime object of the invention to provide an assay method. In fact, $\Delta_5$-3-keto-steroid isomerase lends itself to use as an enzymatic labelling agent all presently known immunoenzymatic assay methods, for example the so-called "double antibody methods", in which the enzymatic activity is measured in solution. However, as has been previously indicated, the particular nature of the enzyme whose application is proposed by the invention enables methods of applying the process of immunoenzymatic assay which are simplified and improved with respect to those previously known.

As such, $\Delta_5$,3-keto-steroid isomerase is a known enzyme. By way of bibliographic references relating to this enzyme, may be mentioned, for example, extracts of the work "Methods in Enzymology" Vol. 5 (1962) p. 527 et seq. (Academic Press) and Vol. 34 (1974) p. 557 et seq. (William B. Jakoby and Meir Wilchek). $\Delta_{5'}$,3-keto-steroid isomerase is an enzyme reputed to be active and giving rise to rapid reactions. The effects that it shows in its application to immunoenzymatic assay were quite unforseeable. In fact, it is not possible to see in advance the behavior of a particular enzyme on its coupling with an antigen or an antibody. It is known, in fact, that certain enzymes have a tendency to be denatured or inactivated in the coupling reaction. In addition, the chemical structure itself of the enzyme poses a particular problem, since it is an enzyme with a hydrophobic site. Various coupling agents, currently used in immunoenzymatic methods, such as glutaraldehyde or phenyl diisocyanate, show themselves to be less suitable for the requirements of the invention. It is to be noted also that the high activity of the enzyme would have rendered impossible the automation of the assay of the invention, whereas, as has been noted previously, the use of $\Delta_5$,3-keto-steroid isomerase enables the assays to be automatized on pre-existing radio-immunological equipment.

The enzyme used according to the invention is the isomerase of the micro-organism *Pseudomonas Testosteroni*. In the Example 1 which follows detailed indications are given on the culture of the micro-organism, the preparation of an acetone power and the purification of the enzyme. The enzyme is purified by chromatography on DEAE cellulose and then affinity chromatography on oestradiol-agarose according to the method described in "Method in Enzymology", Vol. 34 (1974) p. 557 et seq. cited above.

The specific activity of the enzyme used is high, for example, of the order of 30,000 IU/mg to 60,000 IU/mg.

The $\Delta_5$-3-keto-steroid isomerase of *P. Testosteroni* possesses very high specific activity and a low molecular weight (about 25,000): the first property enables assays of a sensitivity never previously attained in immunoenzymology, the second (low molecular weight) enables the realization of labelling of the antigen which preserves good immunoreactivity in the latter.

The activity of the enzyme is determined according to the method described by TALALAY (J. Biol. Chem. 237 (1962), 1500–1506). A unit of activity corresponds to the amount of enzyme isomerizing $1\mu$ Mole of $\Delta_5$-androstene dione per minute at 25° C. and at pH=7. The absorbancy of 1 mole/l of $\Delta_4$-androstene dione in aqueous solution is 16,300 at 248 nm.

The absorbancy of $1\mu$ mole of $\Delta_4$-androstene dione in solution in a reaction medium of 1 ml is equal to:

$$\frac{16,300 \times 10^3}{1 \times 10^6} = 16.3$$

and the activity of the isomerase is given by the formula:

$$Act\ U/ml = D_o \times \frac{1}{16.3}\ \text{where}$$

$D_o$=measured absorbancy.

Solutions containing 1 mg of isomerase per ml have an absorbancy equal to 0.328 at 280 nm, therefore:

$$As\ IU/mg = \frac{D_o}{16.3} \times \frac{0.328}{abs}$$

1 picomole of enzyme in 1 ml will give per minute at 248 nm a variation in absorbancy of 12 absorbancy units, which permits the detection after 10 minutes of incubation of one femtomole of enzyme ($D_o$=0.120).

Thus, the very high specific activity of $\Delta_5$-3-ketosteroid isomerase, used as a labelling agent immunoenzymatic assays, enables the detection of amounts of antigen of the order of a femtomole. Details are given below of a specific example of its application to the assay of placental lactogenic hormone PLH. The results obtained show that the antigen labelled by the isomerase has an immunoreactivity of the same order of magnitude as that of a radioactive hormone used in radioimmunological assay.

The enzyme proposed by the invention has a great advantage for the immunoenzymatic assays of substances at very low concentration possibly present in biological media, such as hypophyseal hormones and plasmatic steroids. Of course, the invention is not limited to the examples of its application which have just been described. In fact, the invention applies to the detection and determination of any sort of fixing proteins and of corresponding conjugate substances.

The invention relates to a method of coupling the enzyme with the antigen which may be of a different nature according to the nature of the antigen, for example, according as it relates to a peptide hormone or a steroid hormone. In all cases, however, the coupling brings into play a thio residue of the enzyme.

Thus, in the case of coupling of $\Delta_5$,3-keto-steroid isomerase with a steroid hormone, the latter, denoted by the abbreviation Ag, is reacted with bromoacetic acid of the formula Br—$CH_2$—COOH in the presence of carbodiimide. In addition, the enzyme is converted into an enzyme bearing —SH groups by reaction with S-acetyl-mercapto succinic anhydride. Finally, the hormone bearing the bromo substituent is reacted with the enzyme bearing the —SH groups, the whole of the coupling being carried out in accordance with the following reaction diagram:

The latter reaction being practically quantitative, the coupling effected is very satisfactory.

The number of molecules of antigen bound per molecule of enzyme may easily be determined by spectrophotometry. This method enables the bonding of the antigen molecules to the enzyme to be efficiently checked. In the case of progesterone, it is possible to introduce 2 to 4 molecules of steroid per molecule of enzyme.

In a particularly advantageous embodiment of the invention, there is provided a special coupling method in the case of peptide hormones. In this case, in fact, the coupling with the peptide hormone is carried out after the introduction of thio residues with the formation of a disulphide bridge. Example 2 below will illustrate the application of this method of coupling to placental lactogenic hormone PLH.

The amidination of PLH by methyl 4-mercaptobutyrimidate enables the introduction of two thiol residues per mole of hormone.

S-acetyl mercaptosuccinic anhydride enables the introduction of 9 thiol residues per mole of enzyme.

The incubation of 0.1 μm of PLH containing 2 thiol residues per mole with 0.05 μm of isomerase containing 9 mixed disulphide groups (dithio-5 (2-nitrobenzoate)-succinamide) leads to the release of 0.1 μm of thionitrobenzoate. The reaction is complete at the end of 4 hours. The enzymatic activity measured at this stage shows that 80% of the starting enzymatic activity is preserved.

In general, the method of coupling proposed by the invention may be represented by the following reaction diagram:

The method of coupling proposed by the invention presents the advantage of not giving rise to the formation of enzyme-antigen high polymers; the coupling yield is high, even for low protein concentrations (0.2 mg/ml). The enzyme may be liberated from the antigen-antibody complex and its enzymatic activity may thus be measured in a homogeneous phase, which enables the accuracy of measurement to be increased. To free the enzyme, it is sufficient react the antigen-antibody complex, bearing the enzyme, with a reducing agent, such as dithiotreitol or β-mercaptoethanol.

The antigen-enzyme coupling proposed by the invention is stable under normal conditions. There is no liberation by the seric proteins. In addition, the coupling is stoichiometric: one mole of antigen is bound to one mole of enzyme. It is observed that the enzyme coupled to the antigen is stable over at least one year at 4° C.

Within the scope of the present invention, coupling tests have been carried out to compare the results obtained with various known coupling reactants and with the reactants according to the invention, which enables a linkage through a disulphide bridge to be effected. In all the tests, $\Delta_5$,3-keto-steroid isomerase was used as the enzyme for the coupling. The coupling yield was then measured, that is to say the percentage of substance coupled to the isomerase, as well as the residual enzymatic activity of the coupled product. The known reactants used by way of comparison were: glutaraldehyde, (at concentrations of 2%, and of 0.02% by weight), phenyl diisocyanate (at pH 7 and at pH 5) and dimethylsuberimidate.

Coupling tests of $\Delta_5$,3-keto steroid isomerase with placental lactogenic hormone were carried out in a single step with glutaraldehyde according to the following procedure: 1 mg of PLH and 1 mg of $\Delta_5$,3-keto steroid isomerase, in solution in 1 ml of phosphate buffer at pH 7.2, were incubated with 2% or 0.02% of glutaraldehyde at room temperature for 24 hours. After the reaction the conjugates were separated by affinity chromatography on Sepharose oestradiol and then on Sephadex G 100.

The coupling tests with phenyl diisocyanate and with dimethylsuberimidate were carried out after activation of the $\Delta_5$,3-keto-steroid isomerase by the bifunctional reactant (the bifunctional reactant at a concentration of $10^{-2}$ M is incubated for 2 hours at room temperature with $\Delta_5$,3-keto-steroid isomerase ($4.10^{-5}$ M)). After the reaction, the excess of reactant was removed by chromatography on Sepharose oestradiol, the modified enzyme (1 mg) was incubated with 1 mg of placental lactogenic hormone. After reacting for one night at room temperature, the excess hormone is removed by affinity chromatography on Sepharose oestradiol.

The results obtained are contained in Table I.

The results show that glutaraldehyde at high concentration denatures the enzyme applied according to the invention and provides a very poor coupling yield, and that glutaraldehyde at low concentration, whilst partly avoiding the denaturation of the enzyme provides a coupling yield of an order not exceeding 15%. With phenyl diisocyanate at pH 7, the yield is non-existent, whilst at pH 9.65 there is almost total denaturation of the enzyme. With dimethylsuberimidate, partial inactivation is noted and the coupling yield is of the order of 15%.

On the contrary, the coupling provided by the invention enables a high coupling yield to be obtained whilst preserving the greater part of the enzymatic activity. It is seen therefore that such a coupling is well adapted to $\Delta_5$,3-keto-steroid isomerase, while by reason of the particular characteristics of this enzyme, the other coupling reactants, although widely used in enzymatic coupling, are less interesting from the practical point of view.

It will also be noted that the mode of coupling involving a disulphide bridge, such as provided by the invention, could be used with other enzymes useful as labelling agents. In the course of tests carried out within the scope of the present invention, it has however been observed on the one hand that all enzymes are not suitable and, on the other hand, that certain of the enzymes which are suitable give rise subsequently to difficulties in the purification of the obtained conjugate products due to the fact that these enzymes cannot be purified by affinity chromatography. Thus, tests have been conducted with placental lactogenic hormone by adopting the mode of coupling provided by the invention but with various enzymes, namely peroxidase, phosphatase and steroid dehydrogenase by way of known enzyme for comparison, and $\Delta_5$,3-keto steroid isomerase.

The coupling of peroxidase, of phosphatase and of steroid dehydrogenase is carried out after thiolation of these enzymes with S acetyl mercaptosuccinic anhydride (see Example 2 below). The thiol residues are activated in the form of mixed disulphides with dithiobisnitrobenzoate. The activated enzyme is separated from the excess dithiobisnitrobenzoate by chromatography on Sephadex G 25; the fraction containing the activated enzyme is incubated with 1 mg of PLH previously treated with mercaptobutyrimidate (see Example 2). The reaction is followed by spectrometry at 412 nm and the coupling products were separated by chromatography on Sephadex G 100.

The results obtained are gathered in Table II.

The results of Table II show that with the provided coupling method, peroxidase and phosphatase would be principle be usable as labelling agents for immunoenzymatic assays, but the immunoreactivity of the conjugate obtained after purification is not satisfactory. As for dehydrogenase, it cannot be used with this method of coupling, due to the fact of its inhibition by the coupling reactant. It would be the same for enzymes possessing a cystein residue essential for the activity.

It is seen therefore that the mode of coupling of the invention takes into account particular characteristics of $\Delta_5$,3-keto-steroid isomerase. In fact, the combined choice of the latter and of the mode of coupling enables two essential advantages to be achieved simultaneously:
high yield in the production of the conjugates
easy purification, by affinity chromatography, enabling the production of conjugates possessing very high immunoreactivity.

It was indicated previously that, for the immunoenzymatic assay properly so called was possible to use customary methods for example the method called double antibody. Thus, recourse may be had to the procedure already employed for radio-immunological assay, the radioactive hormone having been replaced by the $\Delta_5$,3-keto-steroid isomerase conjugate.

In one embodiment of the invention resorting to conventional means for the assay, after separation and washing by centrifugation, the antigen bound to the immunoadsorbent is incubated. After centrifugation, the enzymatic activity of the supernatant liquor is determined, which can be carried out automatically by means of a spectrophotometer.

The results obtained show also that there exists a good correlation between the immunoenzymatic assay according to the invention and the radio-immunological method. In fact, the accuracy of the measurement, in the case, for example, of placental lactogenic hormone, is at least equal to that provided by a radio-immunological assay.

This observation has been checked for whatever separation method is used, for example the method of insolubilized antibodies or the double antibody method.

It should be noted however that the invention also enables the realization of immunoenzymatic assays under conditions that were not possible hitherto in practice, precisely by reason of the nature of the enzymes used. In all the known methods, in fact, it was customary to use a solid phase, the enzyme being fixed on this support, and then to carry out incubation, for example, for at least 10 minutes. In a good many cases, this method does not permit complete automation of the assay. On the contrary, the particular properties of $\Delta_5$,3-keto-steroid isomerase, as applied according to the invention for immunoenzymatic assays, enables this incubation step to be avoided. Hence, the invention provides a novel assay method in which it suffices to pass the substrate solution over a solid phase containing the insolubilized enzyme. For example, this passage can involve simple filtration or percolation over a support bed such as "Sepharose", containing the insolubilized enzyme. It then suffices to measure the absorbancy of the solution of the substrate after its passage over this solid phase. The one skilled in the art will understand that such an assay procedure lends itself perfectly to

TABLE I

| | Coupling with $\Delta$ 5-3-keto-steroid isomerase 2% | | | | | |
|---|---|---|---|---|---|---|
| | Glutaraldehyde 2% | Glutaraldehyde 0.02% | Phenyldiisocyanate pH = 7 | Phenyldiisocyanate pH = 9.5 | Dimethylsuberimidate | Invention |
| Residual Activity | 10% | 40% | 60% | <5% | 40% | 80 to 70% |
| % PLH coupled to isomerase | <1% | 15% | <0.5% | undetermined | 15% | 60% |

TABLE II

| Coupling of placental lactogenic hormone with different enzymes | | | | |
|---|---|---|---|---|
| | $\Delta$ 5-3-keto-steroid isomerase | Peroxidase | Phosphatase | Steriod dehydrogenase |
| Residual Activity | 70% | 80% | 50% | 30% |
| Immunoreactivity of the conjugate obtained after purification | 90% | 30% | 40% | undetermined |

The variations in absorbancy at 248 nm as a function of the amount of hormone or other substance to be tested enable quantitative assay to be effected.

It must be noted that the enzymatic activity corresponding to non-specific fixation is remarkably low due to the fact that only the enzyme retained specifically by the immunoadsorbent can be liberated, for example by dithiotreitol, whereas the enzyme retained non-specifically remains bound to the phase. This advantage enables the use of the enzyme-antigen preparation directly obtained after affinity chromatography and avoids chromatography on Sephadex G 100 which separates the free enzyme from the conjugated enzyme.

complete automation in particular on equipment already known and used in radio-immunology, for example the apparatus marketed under the name "Centria" by the UNION CARBIDE Company.

It was previously indicated that the use of $\Delta_5$,3-keto-steroid isomerase enables a novel immunoenzymatic assay method to be practised, namely a method not calling upon insolubilized antibodies.

The antigen-enzyme-antibody complex may be separated from the enzyme-antigen by differential precipitation by solvents such as: dioxane, ethanol, methanol, or more particularly polyethylene glycol. The antigen-enzyme conjugate remains in solution and may be assayed directly. This method is applicable to the assay of antigens of low molecular weight ($\leqq 25000$).

The mode of coupling proposed by the invention renders possible such an assay method, since it permits the production of an antigen-enzyme conjugate possessing an immunoreactivity above 50%, or, in other words, it ensures that an enzymatic activity level higher than 50% can be bound to the antibody.

Thus, due to the application of $\Delta_5$,3-keto-steroid isomerase as provided by the invention for immunoenzymatic assays, it is possible not only to carry out traditional assays, but it becomes also possible to practice novel assay methods. Thus, the development of the enzymatic activity bound to the antibodies can be effected by several means:

(1) direct reading on the supernatant liquor or on the cake obtained by precipitation by means of a solvent, such as polyethylene glycol, with the use of soluble antibodies;

(2) read-out in solution after liberation of the enzyme from the antigen-antibody complex by reducing agents such as dithiotreitol;

(3) immediate reading after filtration of a substrate solution on the antibody-antigen-enzyme in solubilized complex.

The foregoing indications will make it sufficiently clear to the one skilled in the art, the advantage of these novel assay methods and the manner of using them.

Whatever the assay method used, the high specific activity of the enzyme enables the application of amounts of the antigen-enzyme complex which occur in the state of traces in the reaction medium. In fact, the immunoreactivity of the complex is comparable with that of the free antigen due to the fact of the low molecular weight of the enzyme and the selectivity of the coupling.

The use for immunoenzymatic assay of $\Delta_5$,3-keto-steroid isomerase presents numerous advantages of which the principal have been summarized as follows:

enzyme of very high specific activity going up to 60,000 IU/mg, which corresponds to a variation in optical density, at 248 nm per minute, of 24,000 milliunits of absorbancy for one picomole, low loss of enzymatic activity in coupling, purification and separation of the complex Ag-Enz from the excess Ag by simple and rapid affinity chromatography, stability of the Ag-Enzyme complex, 0.5 mg of Ag-Enzyme complex enabling the production of almost $10^6$ assays, low molecular weight not reducing the immunoreactivity of the antigen, the development of the enzymatic activity being effected in some minutes, the assay may be quickly automatized in existing equipment for radio-immunology.

The invention will now be illustrated without being in any way limited of course in scope, by the following examples:

EXAMPLE 1

Preparation of $\Delta_5$,3-keto-steroid isomerase

1a. Culture of the micro-organism.

The micro-organism *Pseudomonas Testosteroni* (A.T.C.C. 11996) was cultivated at 30° C. in a liquid medium of the following composition: Difco extract of yeast, 10 g; $(NH_4)_2HPO_4$, 1 g; $(NH_4)H_2PO_4$, 1 g; $KH_2PO_4$, 2 g; and 10 ml of a solution of mineral elements per liter of deionized water. The composition of the mineral solution was: $MgSO_4.7(H_2O)$ 20 g; NaCl; 1 g; $ZnSO_4.7 H_2O$, 0.5 g; $MnSO_4.3 H_2O$, 0.5 g; $CuSO_4.5 H_2O$, 0.05 g; 0.1 N $H_2SO_4$, 10 ml in one liter of distilled water. The final pH was adjusted to 6.65 with 1 N NaOH, and the medium sterilized at 121° C. for 30 minutes. The culture was carried out in tanks of 500 liters capacity, each containing 250 liters of medium. There was added directly 0.2 ml of an antifoaming agent ("Antifoam A-60"-General Electric Company), per liter of culture, and subsequently variable amounts according to the need. The tanks were aerated at a rate of 125 to 250 liters per minute and stirred at the rate of 260 revolutions per minute (rpm). Each tank was seeded with 2.5 liters (1% by volume) of an 18 hour old culture of the micro-organism cultivated on the same medium.

After 7 and a half hours of culture, 75 g of finely powdered progesterone suspended in about 600 ml of 1% "Tween 60" were introduced into each container (300 mg per liter). The culture was then continued for a total period of 23 hours from the time of inoculation.

The contents of the tanks was then cooled, by a flow of water, to 8° to 10° C. The cells were collected by centrifugation at 13,500 r.p.m. in an continuous flow "Sharples" supercentrifuge, having a reservoir of 6 liters capacity. The flow rate was from 2.4 to 2.6 liters per minute, and it permitted the sedimentation of 93 to 94% of the cells. The product of each tank filled the rotor to a third or to a half of its volume. The cellular sediment was finally transferred from the rotor into jars of plastic material of 500 ml capacity and frozen in solid $CO_2$. The yield of wet cellular substance was 1.9 to 2.2 kg per 250 liters of culture medium.

1b. Preparation of acetone powder

The cellular mass obtained according to Example 1a was thawed at 4° C. for about 12 hours and suspended in 1.5 liters of potassium phosphate buffer solution at pH 7.0 for each kilogram of sediment, by treatment in a "Waring Blendor" mixer (4 liters capacity) rotating at reduced speed and for a sufficient time to obtain a suspension of uniformly creamy consistency.

Aliquot amounts of this suspension (250 ml) were then poured, very slowly, into 2.5 liters of acetone at −20° C. contained in the bowl of a "Waring Blendor", whilst the stirring was contined at low speed.

After having combined the suspensions, they were left at −20° C. overnight so as to permit sedimentation of the particles. The greater portion of the supernatant liquor was then removed by suction. The very dense suspension which remained was diluted by an equal volume of acetone at −20° C. and poured into wide stainless steel "Buchner" funnels of 33 cm diameter, supplied by "Commercial Equipment Company", Milwaukee, which had been lined with two sheets of filter paper. The residue was washed with an additional amount of acetone at −20° C. and then with ether also at −20° C.

The cake obtained was then withdrawn from the "Buchner" and dried in a hood, by pressing on a thick sheet of filter paper, so as to convert it into a dry light-powder, and which remains slightly beige in color.

The powder was placed in wide Petri dishes which were kept under vacuum, in a dessicator, until all smell of acetone had disappeared. The powder was finally preserved in a vacuum jar at −20° C. Under these conditions, the enzymatic acitivity was stable for at least a year.

The yield of acetone powder was about 25% of the total weight of the cellular substance obtained by centrifugation.

1c. Purification of the isomerase from the acetone powder.

Figure 1:
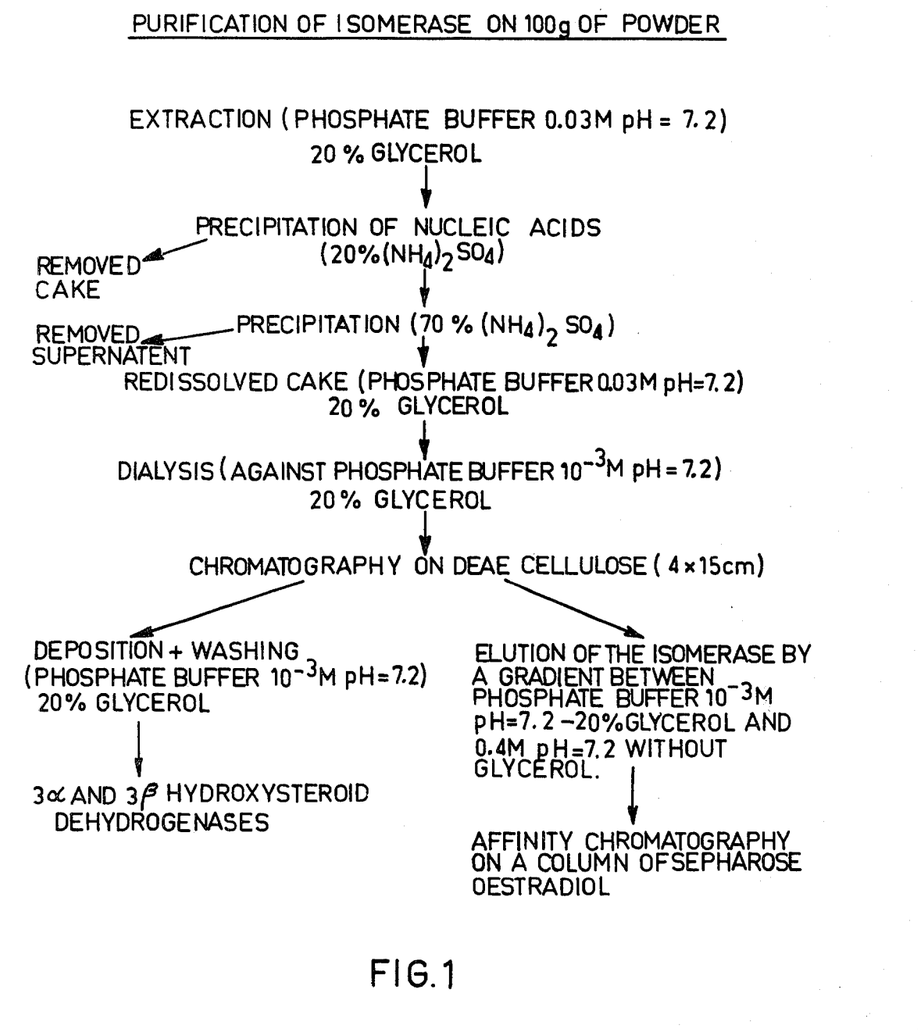

The purification of the isomerase was then effected starting from the acetone powder prepared in accordance with Example 1b. Appended FIG. 1 is a table which summarizes the principal steps of purification, the latter having been done on 100 g of acetone powder. The one skilled in the art will be referred to this figure to obtain all information necessary for him to prepare a $\Delta_5$,3-keto-steroid isomerase of high purity.

Table III below summarizes the results obtained after each of the steps of FIG. 1.

Example I shows that, for 250 l of culture medium, 1.9 to 2.2 kg of wet cellular substance was collected. After treatment of this mass to obtain the acetone powder, the yield was 250 g of powder/kg of cellular substance. From 100 g of acetone powder, 8 mg of isomerase was obtainable having a specific gravity of 30,000 IU/mg.

TABLE III

Purification of isomerase (test on 100 g of powder)

| | Volume | ACT/ML Units | Total Activity | Absorbancy | Specific Activity IU/MG | Total Yield | Purification |
|---|---|---|---|---|---|---|---|
| Extraction | 650 | 1100 | $715 \cdot 10^3$ | 52.3 | 21 | | |
| After precipitation (70% $(NH_4)_2 SO_4$) | 370 | 1840 | $683 \cdot 10^3$ | 41.6 | 44 | 95.5 | 2.1 |
| After dialysis | 450 | 1290 | $580 \cdot 10^3$ | 21.4 | 63.23 | 81.1 | 3.01 |
| After DEAE | 310 | 1860 | $575 \cdot 10^3$ | 11 | 169 | 80.4 | 8.04 |
| After affinity chromatography | 80 | 2900 | $232 \cdot 10^3$ | 0.05 | 30,000 | 30.08 | 1500 |

In this way the isomerase applied according to the invention was obtained with a high specific activity and a low molecular weight (about 25,000).

EXAMPLE 2

Coupling of $\Delta_5$, 3-keto-steroid isomerase with a peptide hormone, placental lactogenic hormone PLH.

2a. Fixing of thiol residues on PLH.

In this example, there was fixed as follows the thiol residues on the PLH by amidination with methyl 4-mercaptobutyrimidate: 2 mg of PLH were dissolved in 300 μl of water brought to pH 9.5 with 100 μl of 0.1 M bicarbonatecarbonate buffer and supplemented with 1.3 mg of methyl 4-mercaptobutyrimidate. After 4 hours of reaction, the solution was dialysed twice against 250 ml of 0.03 M phosphate buffer, pH 7.2, $10^{-6}$ M dithiotreitol (DTT). After dialysis, 50 μl of the reaction solution was sampled and the thiol groups were determined by the "ELLMAN" reactant.

2b. Fixing of dithionitrobenzoate residues on the enzyme.

The dithionitrobenzoate residues were introduced to the enzyme as follows: 1.6 mg of isomerase (total activity: 50,000 IU) contained in 2 ml of a buffer 0.1 M pH 7.2,20% glycerol incubated with 3.5 mg of S-acetylmercaptosuccinic anhydride (SAMSA) for 2 hours at room temperature. Then the solution was dialysed for 2 hours against 200 ml of phosphate buffer 0.03 M pH 7.2 and then for 2 hours against 100 ml of 0.1 M hydroxylamine pH 7.4 $10^{-2}$ M DTT and finally for one night against 1 liter of 0.1 M tris HCl at pH 8 $10^{-6}$ M DTT. The isomerase solution was incubated with $10^{-3}$ M 5,5'-dithiobis (2 nitro benzoate), the absorbancy at 412 nm was determined by means of a Perkin-Elmer spectrophotometer.

2c. PLH-Enzyme coupling.

The modified enzyme was separated from the excess reactant by affinity chromatography on a column of 0.5 ml Sepharose oestradiol 17β. The excess ELLMAN reactant was removed by washing with 30 ml of phosphate buffer 0.1 M pH 7.2. The enzyme was eluted by 2 ml of deionized water containing 20% of glycerol. The enzyme was collected in 1.4 ml which were added directly to the PLH solution previously obtained (0.5 ml), the pH of the solution being brought to 8.6 to facilitate the exchange of the disulphide bridges. The reaction was followed by measurement of the absorbancy of 412 nm due to the liberation of thionitrobenzoate. After incubation overnight the excess PLH was separated from the fraction bound to the enzyme by a further affinity chromatography on Sepharose oestradiol: the excess hormone was removed by washing with 50 ml of phosphate buffer 0.1 M. The free enzyme and the enzyme conjugated to the hormone was eluted by 2 ml of water containing 20% glycerol. The free enzyme can be separated from the conjugated enzyme-hormone by chromatography over Sephadex G 100.

EXAMPLE 3

Immunoenzymatic assay of the PLH

In this example, there were used either insolubilized anti PLH antibodies (marketed by BIOMERIEUX), or the double antibody method (UNION CARBIDE). The procedure which was followed was the same as that proposed by the manufacturer for radio-immunological assay. However, the radioactive hormone was replaced by the hormone-isomerase conjugate prepared in Example 2c. This conjugate was distributed in the proportion of 0.1 IU/tube.

After separation and washing by centrifugation, the antigen bound to the immunoadsorbent is incubated with 100 μl of phosphate buffer $10^{-2}$ M DTT for about 1 hour and then supplemented with 0.9 ml of phosphate buffer 0.03 M containing 100 mg per liter of a detergent product marketed by ICI (USA) under the name "Brij 35".

After centrifugation, the enzymatic activity of the supernatant liquor was determined automatically in the following manner by means of a "Perkin-Elmer" spectrophotometer coupled to a sampler and a Gilson automatic distributer.

500 μl of phosphate buffer 0.03 M pH 7.2 containing 100 mg/liter of Brij 35, 200 ml/liter of ethanol and $4.10^{-4}$ M of $\Delta_5$, androstene-dione were added automatically to 1 ml of the supernatant liquor containing the enzyme. The enzymatic activity was determined by measurement of the absorbancy at 248 nm after 10 minutes of incubation.

Figure 2:
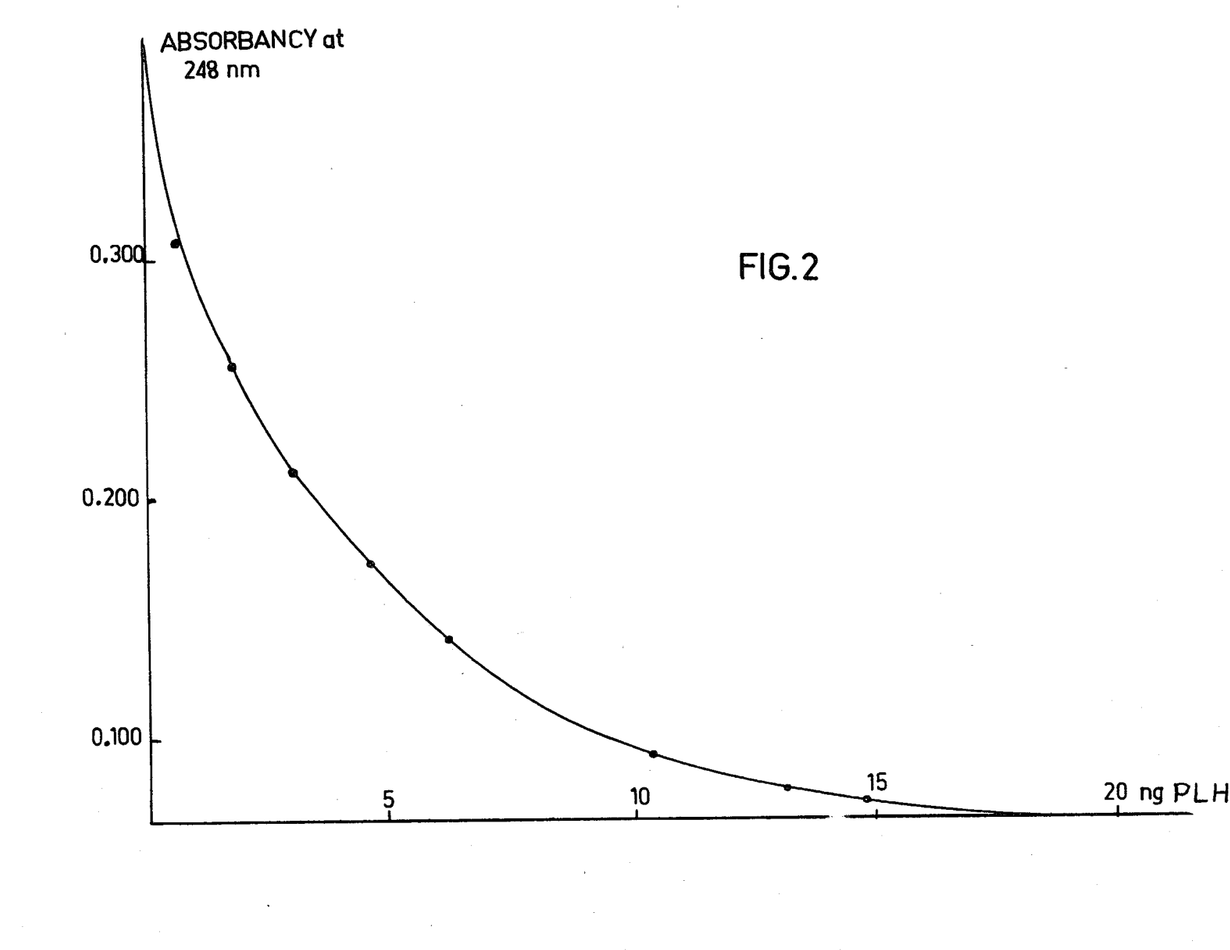
Figure 3:
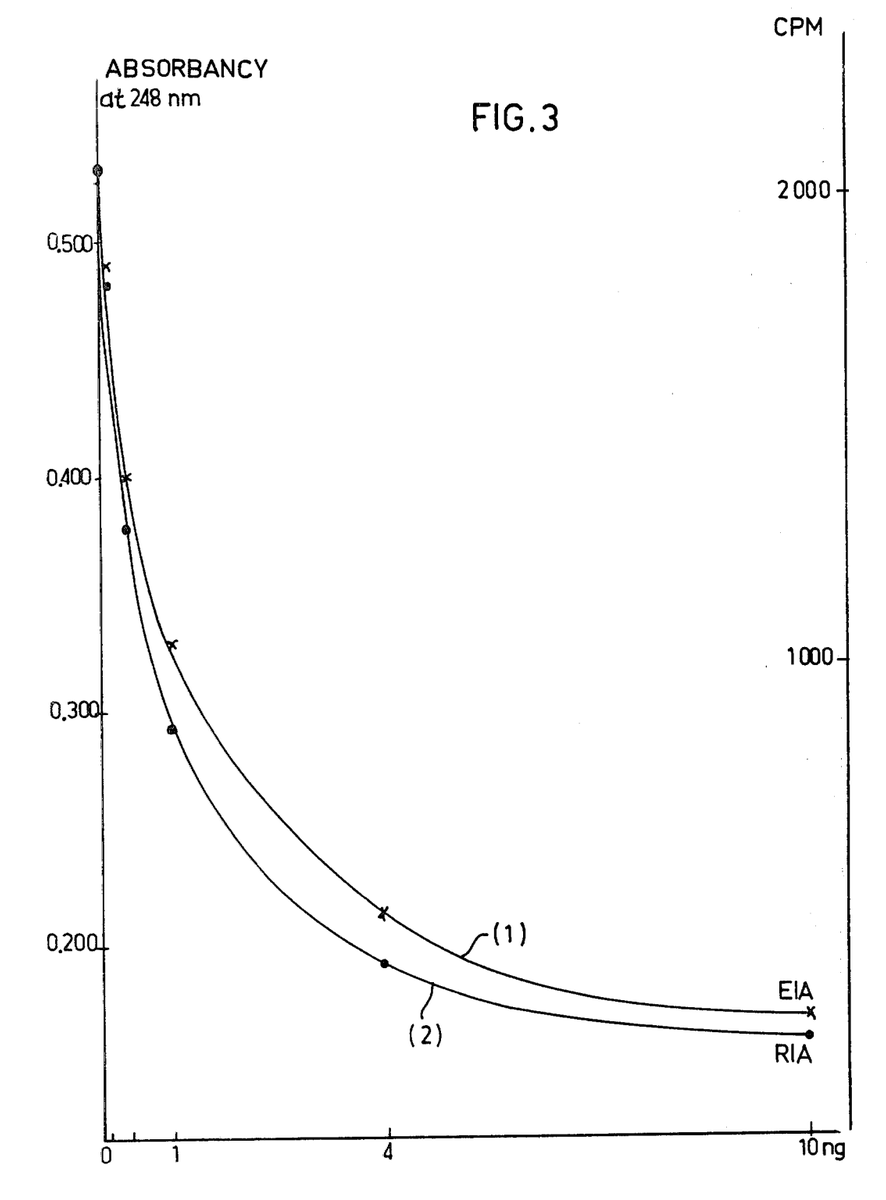
Figure 4:
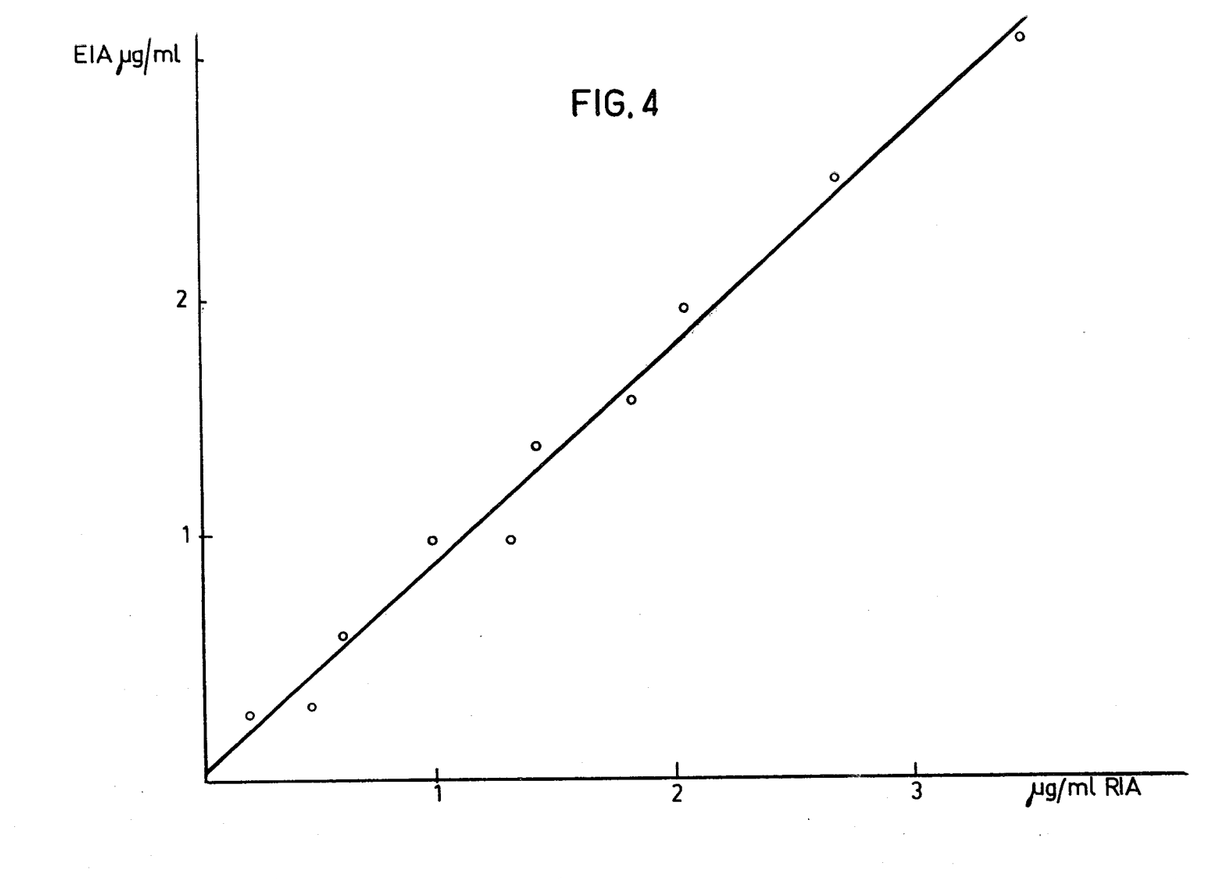

The results obtained are illustrated in FIGS. 2 to 4.

FIG. 2 is a graph illustrating the variation of the absorbancy at 248 nm as a function of the amount of hormone expressed in nanograms. The curve obtained in FIG. 2 results from the assay of PLH with a known method of double antibody assay.

FIG. 3 is a diagram in which there are plotted as abscissae the amount of placental lactogenic hormone annd as ordinates on the one hand the absorbancy at 248 nm according to the results provided by the immunoenzymatic assay of the invention (curve 1 reference EIA) and also the results obtained by a radio-immunological method where the radioactivity was evaluated (in counts per minute cpm), which provided the curve 2 reference RIA.

FIG. 4 is a graph designed to show the good correlation of the results obtained by the immunoenzymatic assay of the invention and those of the radio-immunological method. In this graph are plotted an abscissae the amounts determined by the radio-immunological method and as ordinates the amounts of PLH hormone determined by immunoenzymatic assay.

EXAMPLE 4

Assay of progesterone

4a. Synthesis of the conjugate progesterone-$\Delta_5$, 3-keto-steroid isomerase.

There was first prepared in known manner progesterone 11α-bromoacetate by the technique described in C.R. Acad. Sc. Paris v. 283 (Nov. 8, 1976) Series C, 507-510. In summary, the 11α OH-progesterone was treated with bromoacetic acid using dicyclohexyl-carbodiimide as the coupling agent and tetrahydrofurane as solvent.

In addition, a part of the operational method described in Example 2b was used to fix the -SH groups on the enzyme.

To this end, 1 mg of $\Delta_5$-3-keto-steroid isomerase is used. The isomerase is incubated in 2 ml buffer 0.1 M pH 7.2 20% of glycerol with 3.5 mg of S-acetyl-mercaptosuccinic anhydride (SAMSA) for 2 hours at room temperature. Then the solution is dialysed for 2 hours against 200 ml of phosphate buffer 0.03 M pH 7.2 and then for 2 hours against 100 ml of 0.1 M hydroxylamine pH 7.4 $10^{-2}$ M DTT and finally one night against 1 liter of 0.1 M tris HCl pH 8, $10^{-6}$ M DTT.

For coupling, the isomerase bearing -SH groups is incubated in 1 ml of phosphate buffer 0.03 M, pH 8 with $10^{-4}$ M of progesterone 11α-bromoacetate for 16 hours at room temperature. The excess steroid is removed by repeated dialyses (3 dialyses against 1 liter of phosphate buffer 0.03 M pH 7.2.

4b. Assay of progesterone.

For the assay proper, it is possible to use two methods, either the method of the insolubilized double antibody, or the specific precipitation of the γ globulin fraction by polyethylene glycol.

The anti-progesterone antibodies used (obtained against a 11 hemisuccinate BSA conjugate are those marketed by the Biomerieux firm.

Instead of using a radioactive hormone, as in radioimmunological assays, the hormone isomerase conjugate is utilized in the proportion of 0.05 IU/tube, according to one method or the other.

(1) Method of the double insolubilized antibody.

After incubation and washing the immunoadsorbent, the enzymatic activity bound to the immunoadsorbent is measured by incubation for 5 minutes of the phase with the buffer containing the substrate.

After centrifugation, the absorbancy of the supernatant liquor was measured at 248 nm.

(2) Precipitation by polyethylene glycol.

After incubation of the antibody with the enzyme-progesterone conjugate, obtained in Example 4b, and the sample to be assayed, the γ globulin fraction was precipitated by the addition of a polyethylene glycol solution (final concentration 12.5% by weight).

It was cooled for 45 minutes to 4° C. then the tubes were centrifuged and the enzymatic activity was measured in the supernatant liquor.

Figure 5:
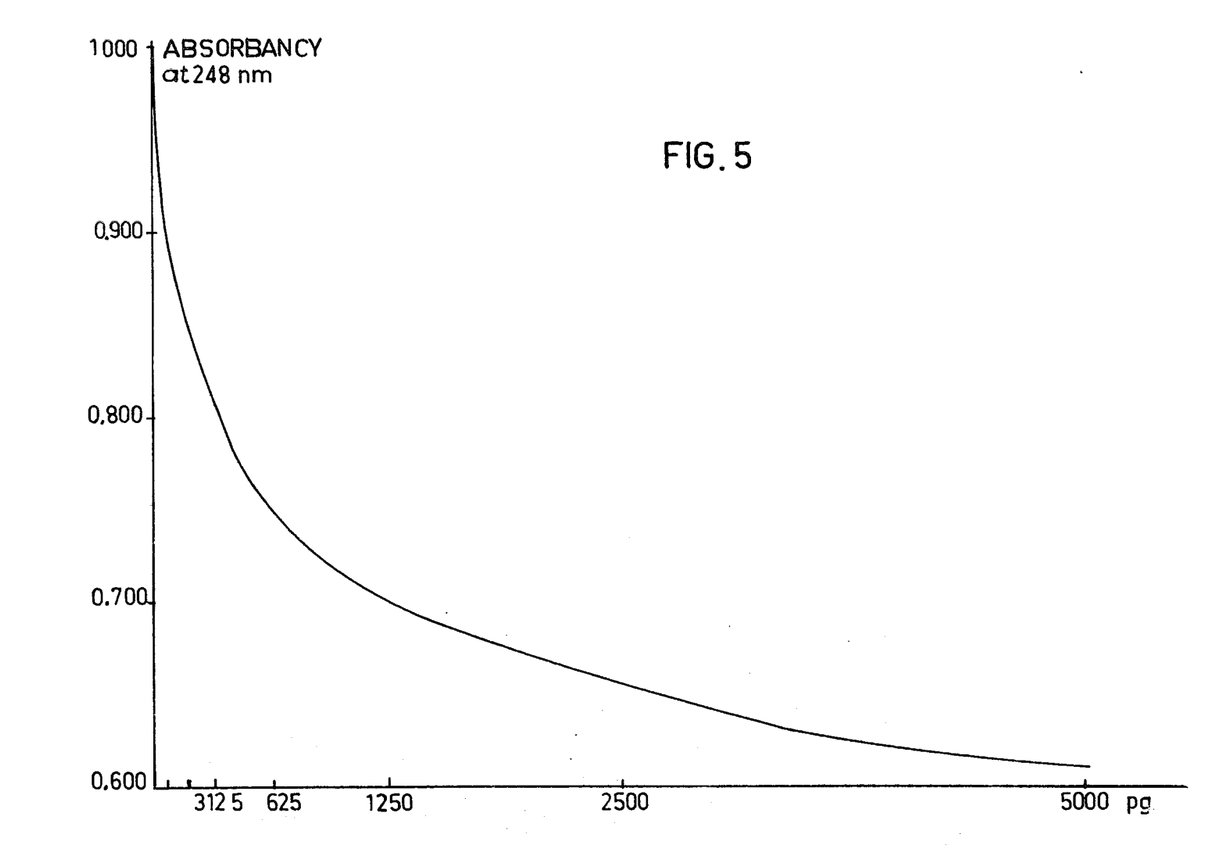

FIG. 5 is a graph in which the results of a representative assay of progesterone by method 4b (1) are plotted. The absorbancy at 248 nm was plotted as ordinates and the concentration of progesterone, expressed in picograms, is plotted as abscissae.

EXAMPLE 5

By means of a particular apparatus marketed by the Union Carbide Company, called "Centria" a direct comparison was made between the radio-immunological assay method, the hormone having been labelled with iodine, and the immunoenzymatic assay method carried out according to the invention, the hormone having been labelled with $\Delta_5$,3-keto-steroid isomerase.

The conditions used for this assay are those recommended by the manufacturer for radio-immunological assay. The antigen conjugated with the isomerase, the antigen and the specific antibodies were incubated for 1 hour.

The antibodies were then retained specifically by an immunoadsorbent (column of Sepharose rabbit anti γ-globulin antibodies). The immunoabsorbent was washed by a buffer containing 1% of detergent (Tween 80). The enzymatic activity bound to the immunoadsorbent was determined by passage of a $10^{-4}$ M solution of $\Delta_5$-androstenedione at the rate of 2 ml in 5 min. The absorbancy at 248 nm of the filtrate was determined by means of a Perkin-Elmer spectrophotometer.

Figure 6:
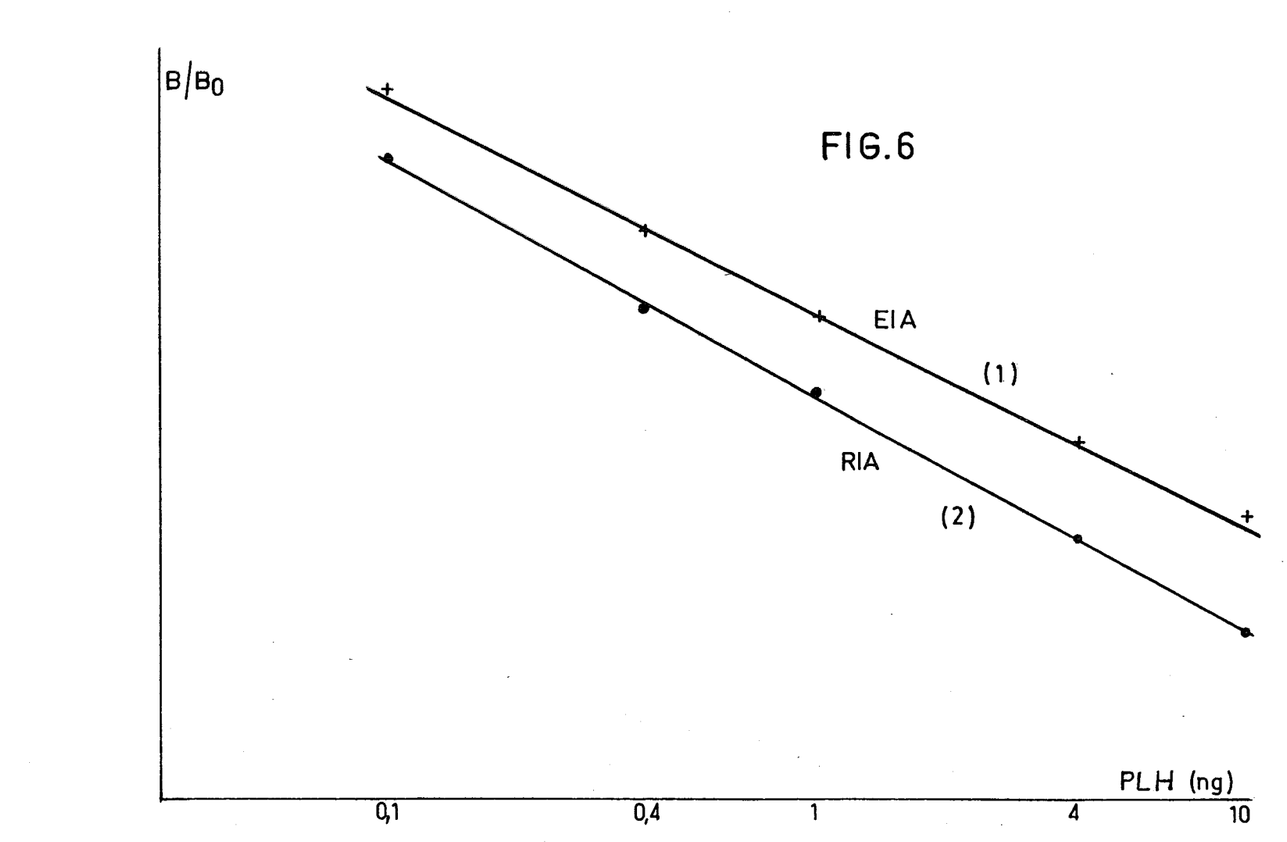

FIG. 6 illustrates the results obtained with placental lactogenic hormone. This example of the application of the method illustrates the facility that the assay according to the invention offers of exploitation by entirely automatic means. A range of concentrations running from 10 ng to 0.1 ng was formed. In this range, the two labelling agents were used simultaneously. The curves obtained are indicated respectively as curve 1 for the immunoenzymatic assay according to the invention and curve 2 for the radio-immunological assay. The results show that the antigen labelled by the isomerase presents little non-specific adsorption and possesses an immunoreactivity comparable with that of the radioactive hormone.

In the graph of FIG. 6, are shown as abscissae the amount of PLH expressed in ng and in ordinates the the ratio B/Bo of the enzymatic or radioactive activity of the bound fraction to the same activity of the fraction bound to the maximum, that is to say in the absence of any antigen.

We claim:

1. In an enzyme immuno assay for a peptide wherein a sample suspected of containing said peptide is admixed with an assay reagent containing an antibody capable of binding said peptide and a peptide-enzyme conjugate under conditions such that a bound species and a free species of said enzyme-conjugate are formed and wherein the enzymatic activity of the bound and/or free species is determined, the improvement comprising: using a $\Delta_5$, 3-keto-steroid isomerase-peptide as the enzyme-peptide conjugate, wherein the conjugate is prepared by reacting the peptide with methyl-4-mercapto-butyrimide, reacting $\Delta_5$, 3-keto-steroid isomerase with S-acetylmercaptosuccinic anhydride; and then coupling the resulting products by a disulfide bridge to form the conjugate containing one mole of peptide and one mole of enzyme.

2. The improved method according to claim 1, wherein the peptide is human placental hormone.

3. The improved method according to claim 1, wherein the immunoenzymatic assay is carried out in homogeneous phase and the $\Delta_5$, 3-keto-steroid isomerase is uncoupled by a reducing agent.

4. The improved method according to claim 3, wherein the reducing agent is dithiotreitol or $\beta$-mercapto-ethanol.

5. The improved method according to claim 1, wherein the admixture is subjected to a differential precipitation with a solvent to separate said bound species from said free species and the activity of $\Delta_5$, 3-keto-steroid isomerase is measured directly on the supernatant liquid or on the precipitate.

6. The improved method according to claim 5, wherein the solvent is selected from the group consisting of polyethylene glycol, dioxane, methanol and ethanol.

7. The improved method according to claim 6, wherein the solvent is polyethylene glycol.

8. The improved method according to claim 5, wherein the peptide has a molecular weight of about 25,000 or less.

9. The improved method according to claim 1, wherein said bound species is immobilized onto a solid phase, a solution containing a substrate for $\Delta_5$, 3-ketosteroid isomerase is passed directly over the solid phase and the absorbancy of the solution is then measured.

10. The improved method according to claim 9, wherein the substrate solution is passed over the solid phase by filtration or percolation.

11. The improved method according to claim 10, wherein the method is carried out by automatic means.

12. In an enzyme immuno assay for a steroid wherein a sample suspected of containing said steroid is admixed with an assay reagent containing an antibody capable of binding said steroid and a steroid-enzyme conjugate under conditions such that a bound species and a free species of said enzyme-conjugate are formed and wherein the enzymatic activity of the bound and/or free species is determined, the improvement comprising: using a $\Delta_5$, 3-keto-steroid isomerase-steroid as the enzyme-steroid conjugate, wherein the conjugate is prepared by reacting the steroid with bromoacetic acid, reacting $\Delta_5$, 3-keto-steroid isomerase with S-acetylmercaptosuccinic anhydride; and then coupling the resulting products by a thiol bridge to form the conjugate.

13. The improved method according to claim 12, wherein the steroid is a steroid hormone.

14. The improved method according to claim 13, wherein the steroid hormone is progesterone.

15. A reagent for use in an enzyme immuno assay for a peptide comprising $\Delta_5$, 3-keto-steroid isomerase from *P. testosteroni*, having free -SH groups and having a specific activity higher than 30,000 IU/mg, coupled to the peptide, wherein coupling to the peptide is effected by reacting the peptide with methyl-4-mercapto-butyrimide, reacting said isomerase with S-acetylmercaptosuccinic anhydride; and then coupling the resulting products by a disulfide bridge to form a conjugate containing one mole of peptide and one mole of enzyme.

16. A reagent for use in an enzyme immuno assay for a steroid comprising $\Delta_5$, 3-keto-steroid isomerase from *P. testosteroni*, having free -SH groups and having a specific activity higher than 30,000 IU/mg, coupled to the steroid, wherein coupling to the steroid is effected by reacting the steroid with bromoacetic acid, reacting said isomerase with S-acetylmercaptosuccinic anhydride; and then coupling the resulting products by a thiol bridge to form a conjugate.

* * * * *